US011405716B2

(12) United States Patent
Freeman et al.

(10) Patent No.: US 11,405,716 B2
(45) Date of Patent: Aug. 2, 2022

(54) MODULAR HEADPHONE SYSTEM

(71) Applicant: Wiley X, Inc., Livermore, CA (US)

(72) Inventors: Daniel W. Freeman, Pleasanton, CA (US); Frank Strauss, Santa Barbara, CA (US); Marc A. Tappeiner, Santa Barbara, CA (US)

(73) Assignee: Wiley X, Inc., Livermore, CA (US)

( * ) Notice: Subject to any disclaimer, the term of this patent is extended or adjusted under 35 U.S.C. 154(b) by 0 days.

(21) Appl. No.: 16/813,300

(22) Filed: Mar. 9, 2020

(65) Prior Publication Data

US 2020/0296501 A1    Sep. 17, 2020

Related U.S. Application Data

(60) Provisional application No. 62/816,762, filed on Mar. 11, 2019.

(51) Int. Cl.
*H04R 1/10* (2006.01)
*H04R 1/28* (2006.01)
*H03F 3/181* (2006.01)

(52) U.S. Cl.
CPC .......... *H04R 1/1083* (2013.01); *H04R 1/105* (2013.01); *H04R 1/1008* (2013.01); *H04R 1/1041* (2013.01); *H04R 1/1075* (2013.01); *H04R 1/288* (2013.01); *H03F 3/181* (2013.01); *H03F 2200/03* (2013.01); *H04R 2201/028* (2013.01)

(58) Field of Classification Search
CPC ........ H04R 5/033; H04R 5/04; H04R 1/1008; H04R 2420/05; H04R 5/0335; H04R 1/1066; H04S 7/304; H04S 7/306

USPC .......................................................... 381/74
See application file for complete search history.

(56) References Cited

U.S. PATENT DOCUMENTS

| 4,499,593 | A | | 2/1985 | Antle | |
|---|---|---|---|---|---|
| 5,382,915 | A | * | 1/1995 | Muri | H03F 3/2171 330/120 |
| 6,466,681 | B1 | | 10/2002 | Siska, Jr. et al. | |
| 8,755,555 | B2 | | 6/2014 | Dougherty et al. | |
| 9,167,338 | B2 | | 10/2015 | Ohlander | |
| 9,226,060 | B2 | | 12/2015 | Minarik et al. | |
| 9,467,767 | B2 | | 10/2016 | Chen | |
| 9,521,480 | B2 | | 12/2016 | Bauman et al. | |

(Continued)

OTHER PUBLICATIONS

PCT/US2020/021847—International Search Report and Written Opinion dated Jun. 3, 2020, 15 pages.

(Continued)

*Primary Examiner* — George C Monikang
(74) *Attorney, Agent, or Firm* — Haynes Beffel & Wolfeld LLP; Andrew Dunlap

(57) ABSTRACT

A modular headphone system that can afford the wearer configurable choices of hearing protection and quality sound delivery for music and programming is provided. In an embodiment, a modular headphone includes a headband and an earpiece mounted to the headband. The earpiece comprises a can comprising a speaker, the can secured to the headband. A removable and replaceable music ear cup is removably mountable to the can to overlie the speaker. A removable and replaceable hearing protection/sound amplification (HP/amp) ear cup is removably mountable to the can to overlie the speaker.

16 Claims, 6 Drawing Sheets

(56) References Cited

U.S. PATENT DOCUMENTS

| | | |
|---|---|---|
| 2011/0108359 A1* | 5/2011 | Nishimura ........... G10K 11/168 |
| | | 181/290 |
| 2013/0153328 A1 | 6/2013 | Carolan et al. |
| 2014/0112520 A1 | 4/2014 | Knudsen |
| 2014/0301577 A1* | 10/2014 | Togawa .................... H03F 3/68 |
| | | 381/120 |
| 2015/0281821 A1 | 10/2015 | Oishi |
| 2016/0175155 A1 | 6/2016 | Jenkins |
| 2017/0200444 A1 | 7/2017 | O'Connell et al. |
| 2017/0264984 A1 | 9/2017 | Pelland |
| 2019/0069873 A1* | 3/2019 | Copt ...................... A61B 7/003 |

OTHER PUBLICATIONS

Maxim Technologies Inc., "Noise Reduction Coefficient (NRC) Test Performed on R-200 U-Charcoal-Mini-Sonex Acoustical Foam Panels", Project No. 3013 71-5070-1, Client Purchase Order No. 13458, Sep. 3, 1997, 3 pages.

PCT/US2020/021847—Second Written Opinion dated Feb. 5, 2021, 8 pages.

PCT/US2020/021847—Amendment under Article 34 filed Jan. 8, 2021, 16 pages.

PCT/US2020/021847—Second Amendment under Article 34 filed Mar. 31, 2021, 17 pages.

\* cited by examiner

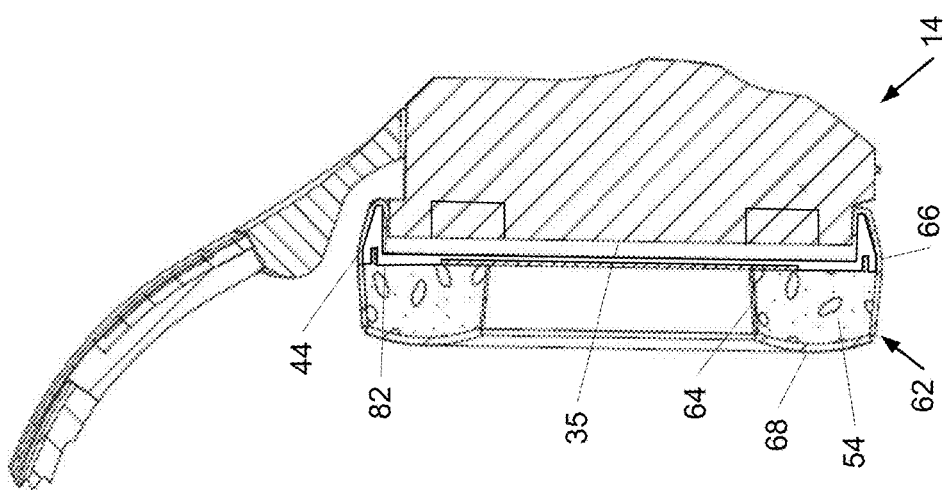
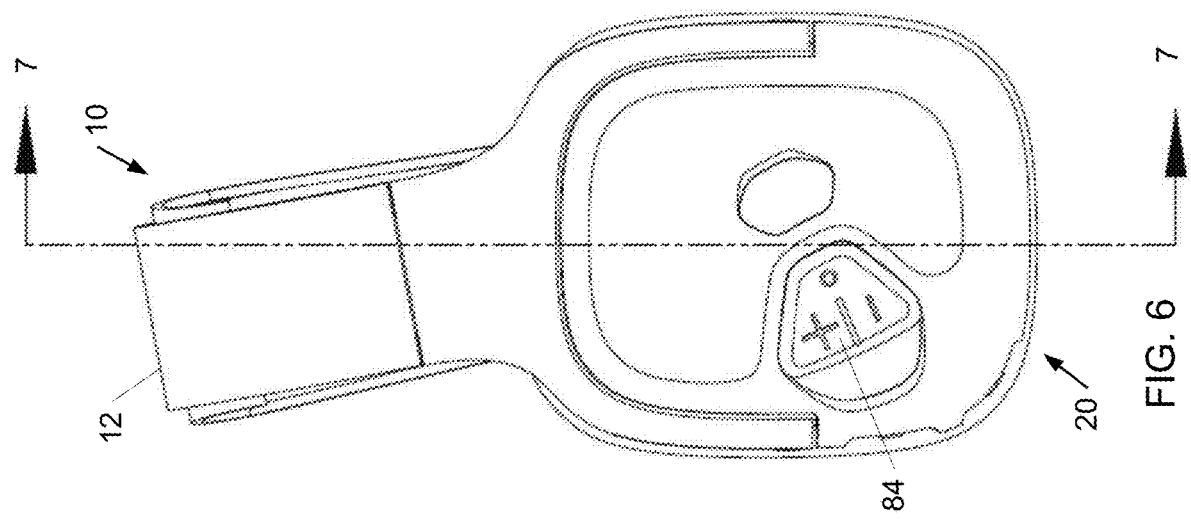

MODULAR HEADPHONE SYSTEM

PRIORITY DATA

This application claims the benefit of U.S. Provisional Patent Application No. 62/816,762, entitled, "MODULAR HEADPHONE SYSTEM," filed on Mar. 11, 2019. The provisional application is hereby incorporated by reference for all purposes.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves may also correspond to implementations of the claimed technology.

Headphones are used for a number of different purposes. One purpose is to provide hearing protection. The most basic hearing protection (HP) headphones are over the ear headphones having ear cups which surround the user's ears to provide passive HP, also called soundproofing. Passive HP headphones filter out ambient noise and also provide an amount of impulse noise protection. Passive HP headphones typically have no electronics.

Another purpose is to deliver sound directly to the user's ear, such as when listening to sounds, both live and prerecorded, including, for example, music, prerecorded books, and telephone conversations. These sound delivery headphones will usually be referred to as music headphones for simplicity. Some music headphones include electronics to provide the user with high-quality music. Over the ear music headphones, because they surround the ear, also filter out ambient noise and provide a limited amount of noise protection.

Both HP devices and music headphones can include electronics to provide conventional noise cancellation, which is particularly effective at generating sound waveforms which are the exact opposite of lower frequency ambient sound waveforms, thus canceling them. However, there is yet no integrated headphone solution that provides the wearer configurable choices of hearing protection and quality sound delivery for music and programming.

BRIEF SUMMARY

A simplified summary is provided herein to help enable a basic or general understanding of various aspects of exemplary, non-limiting implementations that follow in the more detailed description and the accompanying drawings. This summary is not intended, however, as an extensive or exhaustive overview. Instead, the sole purpose of this summary is to present some concepts related to some exemplary non-limiting implementations in a simplified form as a prelude to the more detailed description of the various implementations that follow.

A modular headphone system that can afford the wearer configurable choices of hearing protection and quality sound delivery for music and programming is provided. In an embodiment, a modular headphone includes a headband and an earpiece mounted to the headband. The earpiece comprises a can comprising a speaker, the can secured to the headband. A removable and replaceable music ear cup is removably mountable to the can to overlie the speaker. A removable and replaceable hearing protection/sound amplification (HP/amp) ear cup is removably mountable to the can to overlie the speaker.

The can comprises a can body. In embodiments, the can body comprises a circumferentially-extending side wall surrounding the speaker and a circumferentially-extending open region defined between the speaker and the side wall. In one exemplary embodiment, the HP/amp ear cup comprises a sound absorbing element within the circumferentially extending open region and a sound absorbing layer overlying the sound absorbing element and the speaker. In an exemplary embodiment, each of the music ear cup and the HP/amp ear cup comprise an understructure having a circumferentially-extending outer portion defining an open region aligned with the speaker, and a cushion structure mounted to the understructure, so that the cushion structure defining an ear-receiving open region aligned with the open region of the understructure.

An exemplary cushion structure can comprise a resilient, circumferentially extending, cushion structure body having an inner, circumferentially extending surface, an outer, circumferentially extending surface, and a face surface joining the inner and outer circumferentially extending surfaces. A body cover that covers the inner and outer circumferentially extending surfaces and the face surface can also be part of the cushion structure. In one exemplary implementation, the cushion structure body is made of polyurethane memory foam and the body cover is made of polyurethane synthetic leather. The cushion structure further comprises a sound-permeable cover overlying the open region of the understructure.

An exemplary HP/amp ear cup comprises a sound absorbing element within the circumferentially extending open region and a sound absorbing layer overlying the sound absorbing element and the speaker. The sound absorbing element is made of one or more of polyurethane foam, cotton, melamine, or composite materials. Combinations of these materials, other materials and combinations thereof are contemplated by the disclosed technology. One exemplary headphone employs sound absorbing element is 5 mm to 15 mm thick. In another exemplary headphone, the sound layer is made of one or more of polyurethane foam, cotton, melamine, or composite materials and sound absorbing layer is 2 mm to 4 mm thick.

In one embodiment, amplification circuitry in the HP/amp ear cup ceases sound amplification in response to an impulse sound. The amplification circuitry in the HP/amp ear cup can cease sound amplification in response to an impulse sound exceeding an adjustable threshold. For example, the amplification circuitry in the HP/amp ear cup ceases sound amplification in response to an impulse sound exceeding a level of 82 dB. The amplification circuitry in the HP/amp ear cup can resume sound amplification within 2 milliseconds. Some implementations further including a toggle enabling a user to selectively activate capability of the amplification circuitry in the HP/am ear cup to cease amplification upon detection of an impulse sound.

In another embodiment, a headphone system comprises a headband and an earpiece mounted to the headband. The earpiece comprises a can that includes a speaker. The can is secured to the headband. A hearing protection/sound amplification (HP/amp) ear cup is mounted to the can to overlie the speaker. The can also comprises a can body. The can body comprises a circumferentially-extending side wall surrounding the speaker. A circumferentially-extending region is defined within an inner region defined between the speaker and the side wall. The ear cup comprises a sound-absorbing element within the circumferentially-extending region, a sound-absorbing layer overlying the sound absorbing element and the speaker, and an outer ear cup structure that is configured to engage a user's ear and mounted to the can and overlying the sound-absorbing layer.

One example of the headphone system, the outer ear cup structure comprises an understructure having a circumferentially-extending outer portion defining an open region aligned with the speaker and a cushion structure mounted to the understructure, such that the cushion structure defines an ear-receiving open region aligned with the open region of the understructure. The cushion structure further includes a resilient, circumferentially extending, cushion structure body having an inner, circumferentially extending surface, an outer, circumferentially extending surface, and a face surface joining the inner and outer circumferentially extending surfaces. A body cover that covers the inner and outer circumferentially extending surfaces and the face surface is also part of the cushion structure. Further, a sound-permeable cover overlies the open region of the understructure. Other features, aspects and advantages of technology disclosed can be seen on review the drawings, the detailed description, and the claims, which follow.

BRIEF DESCRIPTION OF THE DRAWINGS

The included drawings are for illustrative purposes and serve only to provide examples of possible structures and process operations for one or more implementations of this disclosure. These drawings in no way limit any changes in form and detail that may be made by one skilled in the art without departing from the spirit and scope of this disclosure. A more complete understanding of the subject matter may be derived by referring to the detailed description and claims when considered in conjunction with the following figures, wherein like reference numbers refer to similar elements throughout the figures.

FIG. 6 is a side elevation view of the left, HP/amp ear piece of FIG. 1.

FIG. 7 is a somewhat simplified cross-sectional view of the structure of FIG. 6 taken along line 7-7.

DETAILED DESCRIPTION

Figure 1:
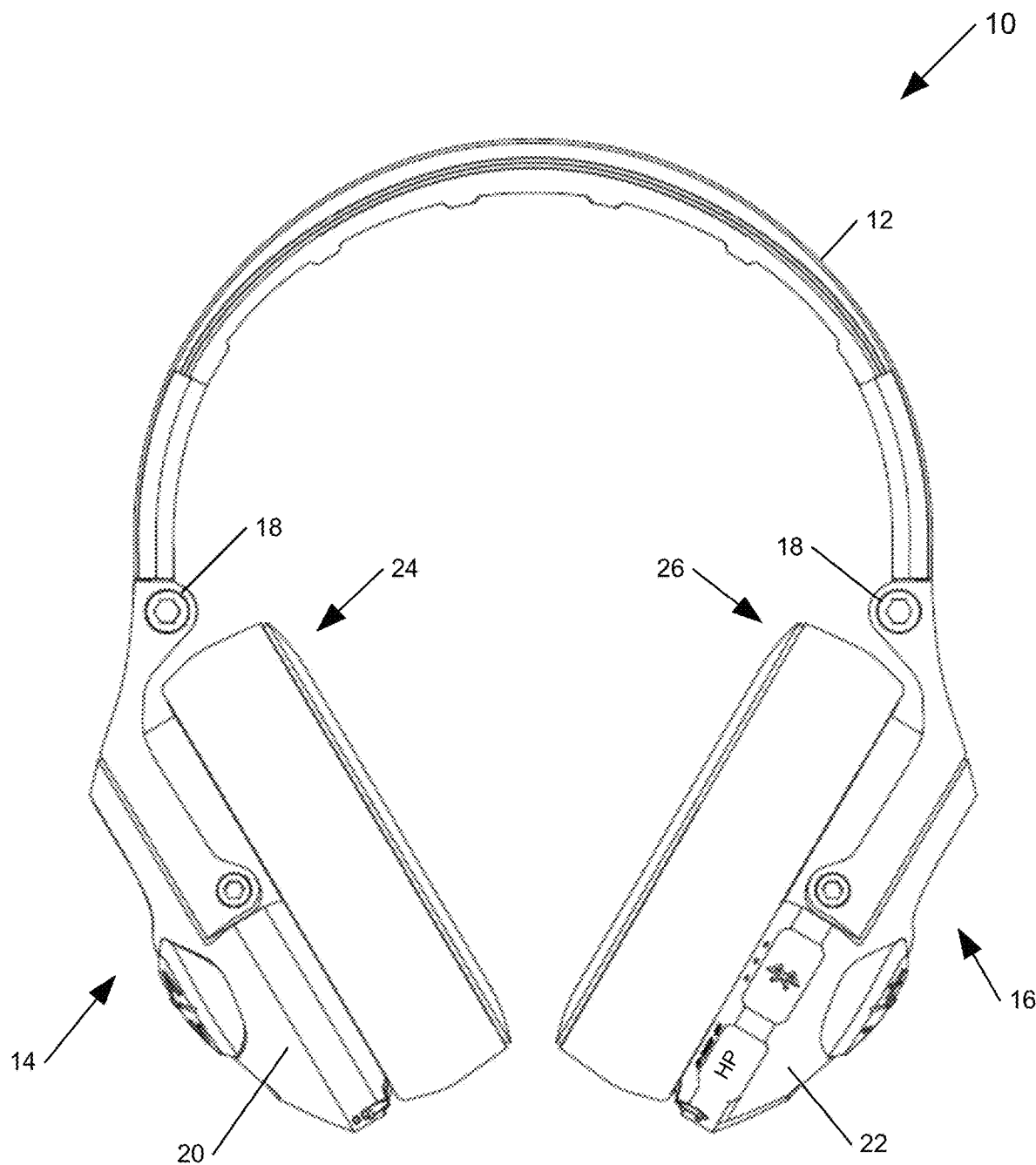
FIG. 1 is a front elevation view of a modular headphone system with removable and replaceable ear cups, the left earpiece having an HP/amp ear cup and the right earpiece having a music ear cup.

The following description will typically be with reference to specific structural embodiments and methods. It is to be understood that there is no intention to be limited to the specifically disclosed embodiments and methods but that other features, elements, methods and embodiments may be used for implementations of this disclosure. Preferred embodiments are described to illustrate the technology disclosed, not to limit its scope, which is defined by the claims. Those of ordinary skill in the art will recognize a variety of equivalent variations on the description that follows. Unless otherwise stated, in this application specified relationships, such as parallel to, aligned with, or in the same plane as, mean that the specified relationships are within limitations of manufacturing processes and within manufacturing variations. When components are described as being coupled, connected, being in contact or contacting one another, they need not be physically directly touching one another unless specifically described as such. Like elements in various embodiments are commonly referred to with like reference numerals.

A more sophisticated version of hearing protection is provided by HP and amplification headphones, which will usually be referred to as HP/amp headphones. HP/amp headphones provide passive hearing protection from loud noises much like passive HP headphones. Some implementations of HP/amp devices also include electronics to amplify relatively low level ambient sound. The passive hearing protection allows the wearer to be protected against sudden impulse sound, such as loud noises in excess of 82 dB, in an industrial or manufacturing setting or loud noises produced by gunfire when hunting. In both cases the HP/amp devices allows the wearer to hear coworkers or hunting companions while being protected against loud, impulse sounds. The electronics are designed so that they do not amplify impulse sounds or other loud sounds. However they can provide enhanced hearing for the low level ambient sounds, such as to permit a hunter to hear sounds of animals as well as speech.

FIG. 1 illustrates one example of a modular headphone system 10 including a headband 12, a left earpiece 14 and a right earpiece 16 secured to headband 12, in this example by a pivot/swivel joint 18. Each ear piece of modular headphone system 10 can be used in a hearing protection/sound amplification (HP/amp) mode or in a music headphone mode. Each earpiece includes what is referred to herein as a can and an ear cup mounted to the can.

Generally, with the present technology a headphone system includes two different interchangeable ear cups mountable to the cans of the earpieces. An HP/amp ear cup to be used when the system is to be used in an HP/amp device mode and a music ear cup when the system is to be used in a music headphone mode. With the present technology electronics for use in two alternative modes, an HP/amp device mode or in a music headphone mode, can be included in the cans. Also, the provision of extra sound deadening material between the can and the users ear, in the examples below provided by a sound absorbing layer in front of the speaker and a sound absorbing element around the speaker, can improve the passive HP against the effects of impulse sounds or other loud sounds in the HP/amp device mode.

In the example discussed below, each can includes the electronics for the speaker/driver. The electronics appropriate for use in the HP/amp device mode and in the music headphone mode can be distributed between the cans or each can include all the necessary electronics. An example of electronics suitable for use in implementing the HP/amp mode is found at FIG. 8: HP/amp audio driver 805. An example of electronics suitable for use in the music mode is found at FIG. 8: music audio driver 804. When the electronics are distributed between the cans, the electronics would be coupled to one another by wires, wireless communications, or both.

Each can 20, 22 preferably can be used with one of two removable and replaceable ear cups, HP/amp ear cup 24 and music ear cup 26. The user chooses which ear cup to mount to the cans 20, 22 based on the mode the system is to be used in. For example, if the system is to be used in a noisy industrial environment or at a shooting range, the HP/amp ear cup 24 would likely be chosen and mounted to each can 20, 22. If the system is to be used, for example, while listening to music or watching a video on an airplane, the music ear cup 26 would typically be used. Modular headphone system 10 shown in the attached figures shows an HP/amp ear cup 24 mounted to the can 20 of the left earpiece 14 and the music ear cup 26 mounted to the can 22 of right earpiece 16 to avoid unnecessary duplication of drawing figures; during use the same type of ear cup, that is HP amp ear cup 24 or music ear cup 26, would typically be used at the same time for both left and right ear pieces 14, 16. Therefore, modular headphone system 10 can be used with two different interchangeable ear cups, the HP/amp ear cup 24 to be used when the system is to be used in an HP/amp device mode and the music ear cup 26 when the system is to be used in a music headphone mode.

Figure 2:
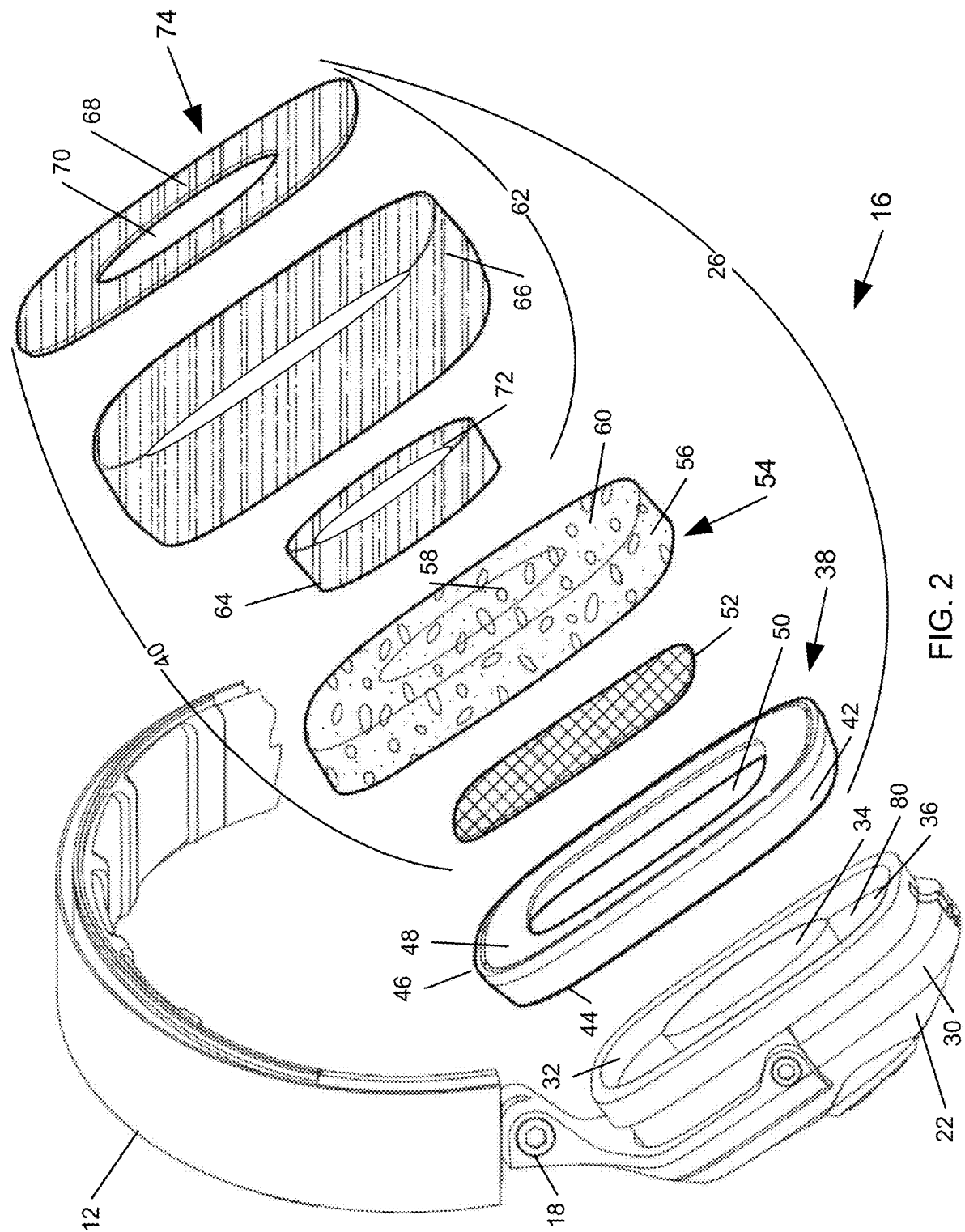
FIG. 2 is an exploded perspective view of the music ear cup of the right, music earpiece of FIG. 1.
Figure 4:
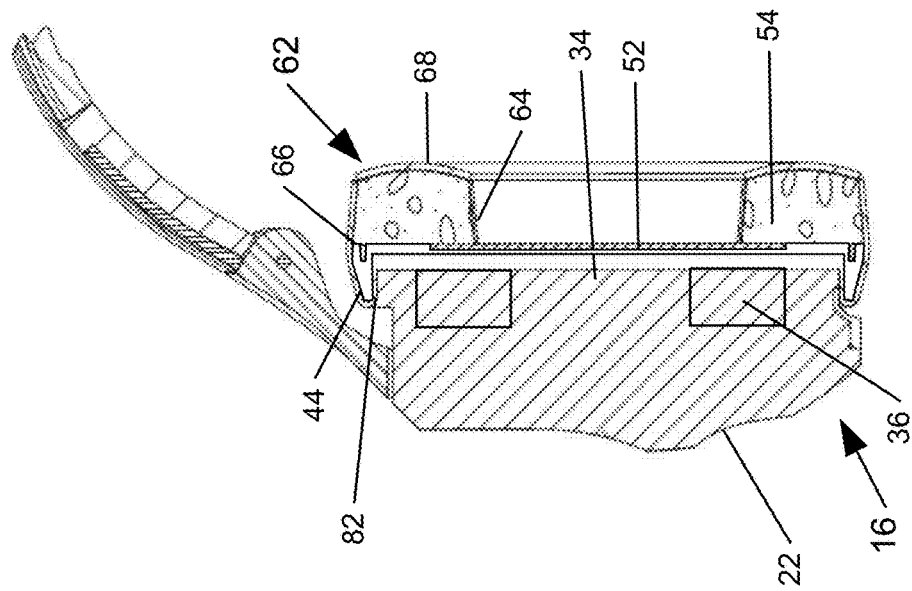
FIG. 4 is a somewhat simplified cross-sectional view of the structure of FIG. 3 taken along line 4-4.
Figure 3:
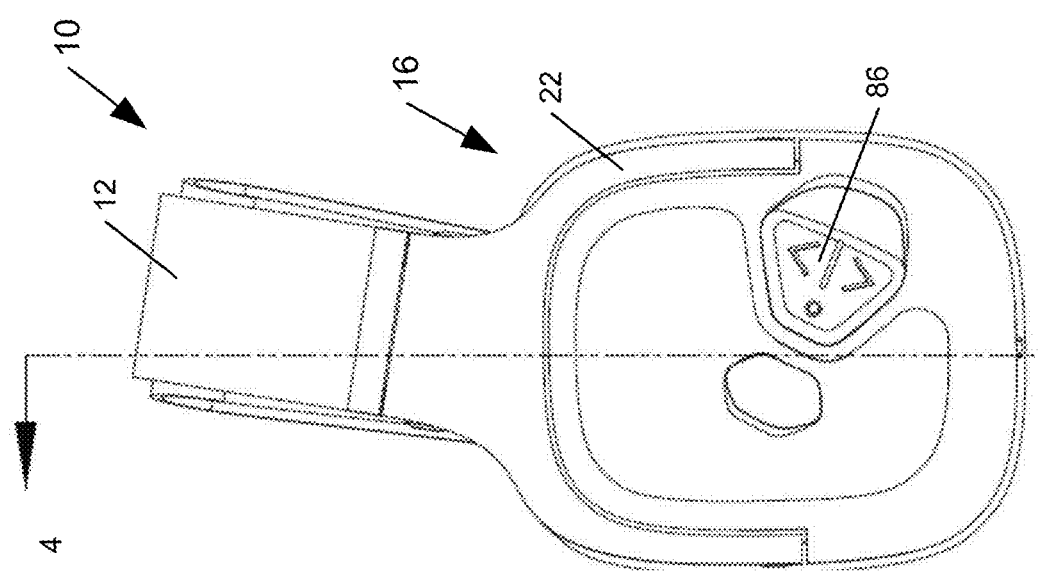
FIG. 3 is a side elevation view of the right, music earpiece of FIG. 1.

FIGS. 2, 3 and 4 illustrate can 22 and music ear cup 26 of the right earpiece 16 of FIG. 1, with components of music ear cup 26 shown in an exploded view in FIG. 4. With renewed reference to FIG. 2, can 22 includes a can body 30 having a circumferentially extending side wall 32 which surrounds a speaker 34 to define a circumferentially extending region 36 therebetween. Ear cup 26 is mountable to and removable from can 22 and includes an understructure 38 and a cushion structure 40. Understructure 38 includes a rim 42 having a first edge 44 towards can 20 and a second edge 46. Understructure 38 also has an inwardly extending flange (or outer portion) 48 extending inwardly from second edge 46. Flange 48 defines an open region 50 aligned with speaker 34.

Cushion structure 40 includes a sound-permeable cover 52 aligned with open region 50. Cover 52 can be made of a fabric material, such as for example and without limitation, non-woven fabrics and materials, staple short fiber and continuous long fibers, that can be bonded together by chemical, mechanical heat or solvent treatments. The amount of sound attenuation provided by cover 52 is preferably no more than 1 dB. Cushion structure 40 also includes a cushion structure body 54 typically made of a foam material such as memory foam comprising mainly of Polyuethane treated chemically to increase its viscosity and/or density, such as for example Reicofil™ available from Reifenhauser Company located in Troisdorf Germany (http://www.reicofil.com/) or equivalent, for a comfortable fit during use. Body 54 has an outer, circumferentially extending surface 56, an inner, circumferentially extending surface 58 and a face surface 60 joining the inner and outer surfaces 56, 58. Cushion structure 40 further includes a body cover 62 including an inner ring member 64 sized to fit within and adjacent to surface 58 of body 54, a circumferential member 66 sized to surround and lie adjacent to outer surface 56 of body 54 and rim 42 of understructure 38, and an end member 68 joined to inner ring member 64 and circumferential member 66; this is illustrated in FIG. 4. The components of body cover 62 are illustrated in FIG. 2 as separate components but are, in this example, a single component. End member 68 has an opening 70 corresponding to the open interior 72 of inner ring member 64, both of which are aligned with open region 50.

Cushion structure 40 defines an ear-receiving open region 74 aligned with open region 50 of understructure 38. Body cover 62 can be made of materials which are nonporous, to facilitate cleaning of cushion structure 40; one suitable example is polyurethane, or polyvinyl chloride, which can be formed to simulate leather. In general, body 54 and body cover 62 are made of materials which are suitable for the expected use environments and are comfortable to wear. As seen in FIG. 4, circumferential member 66 has a re-curved portion 82 which engages first edge 44 of rim 42 to secure cushion structure 40 to understructure 38. The flexibility of circumferential member 66 also permits cushion structure 40 to be removed and permits cushion structure body 54 and sound permeable cover 52 to be cleaned, repaired or replaced as needed.

Figure 5:
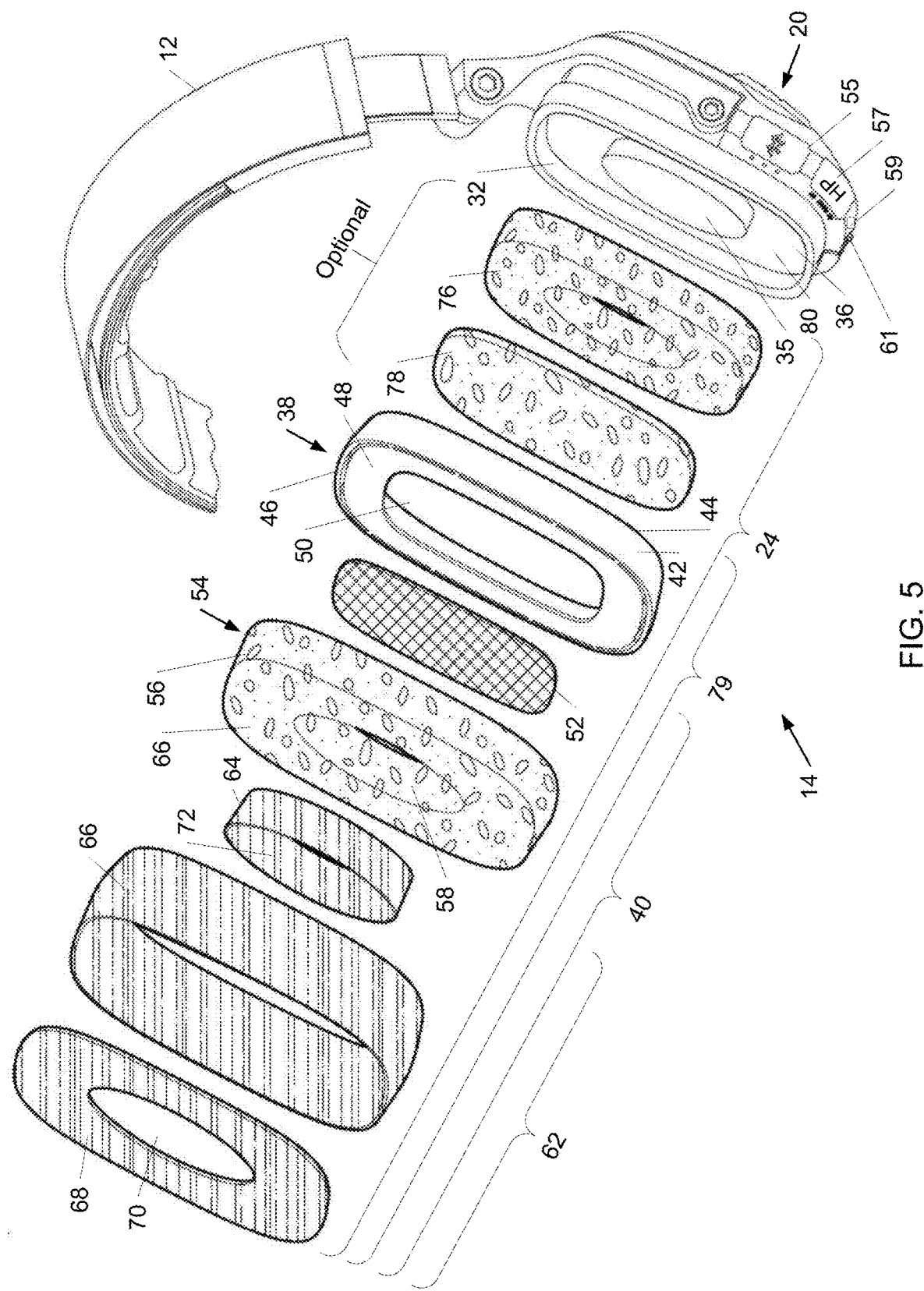
FIG. 5 is an exploded perspective view of the HP/amp ear cup of the left, HP/amp ear piece of FIG. 1.

Left earpiece 14, including can 20 is depicted with HP/amp ear cup 24, in the example that will now be discussed with reference to FIGS. 5, 6, and 7. The portions of can 20 and can 22 engaging ear cups 24, 26 are essentially the same. The primary difference between the HP/amp ear cup 24 of FIG. 5 and the music ear cup 26 of FIG. 2 is the circuitry used to implement the audio drivers 804, 805. In addition, a sound absorbing element 76 and a sound absorbing layer 78 can be incorporated into HP/amp ear cup 24. HP/amp ear cup 24 includes outer ear cap structure 79 which, in this example, is identical to music ear cup 26 so those components will not be described again. In this example sound absorbing layer 78 is positioned between sound absorbing element 76 and flange 48 of understructure 38. Body 30 has an inwardly directed wall 80 extending between the speaker 35 and side wall 32. Sound absorbing element 76 is housed within the circumferentially extending region 36 of can 22 and lies against wall 80. Sound absorbing element 76 and sound absorbing layer 78 are made of materials which enhance the passive hearing protection provided by modular headphone system 10, especially in relation to loud noises, typically in excess of 82 dB, both impulse and non-impulse sounds. In one example sound absorbing element 76 is made of one or more of polyurethane foam, cotton, melamine, or composites thereof about 5 mm-15 mm thick and sound absorbing layer 78 is made of analogous material about 2 mm-4 mm thick. One example material for implementing sound absorbing element 76 and sound absorbing layer 78, Sonex™ was tested to yield a Noise Reduction Coefficient (NRC) equal to 0.65 sound attenuation. In comparing FIGS. 2 and 5, it is seen that circumferentially extending region 36 is an open region in the music ear cup 26 of FIG. 2 while it is substantially filled with sound absorbing element 76 in the HP/amp ear cup 24 of FIG. 5.

Figure 8:
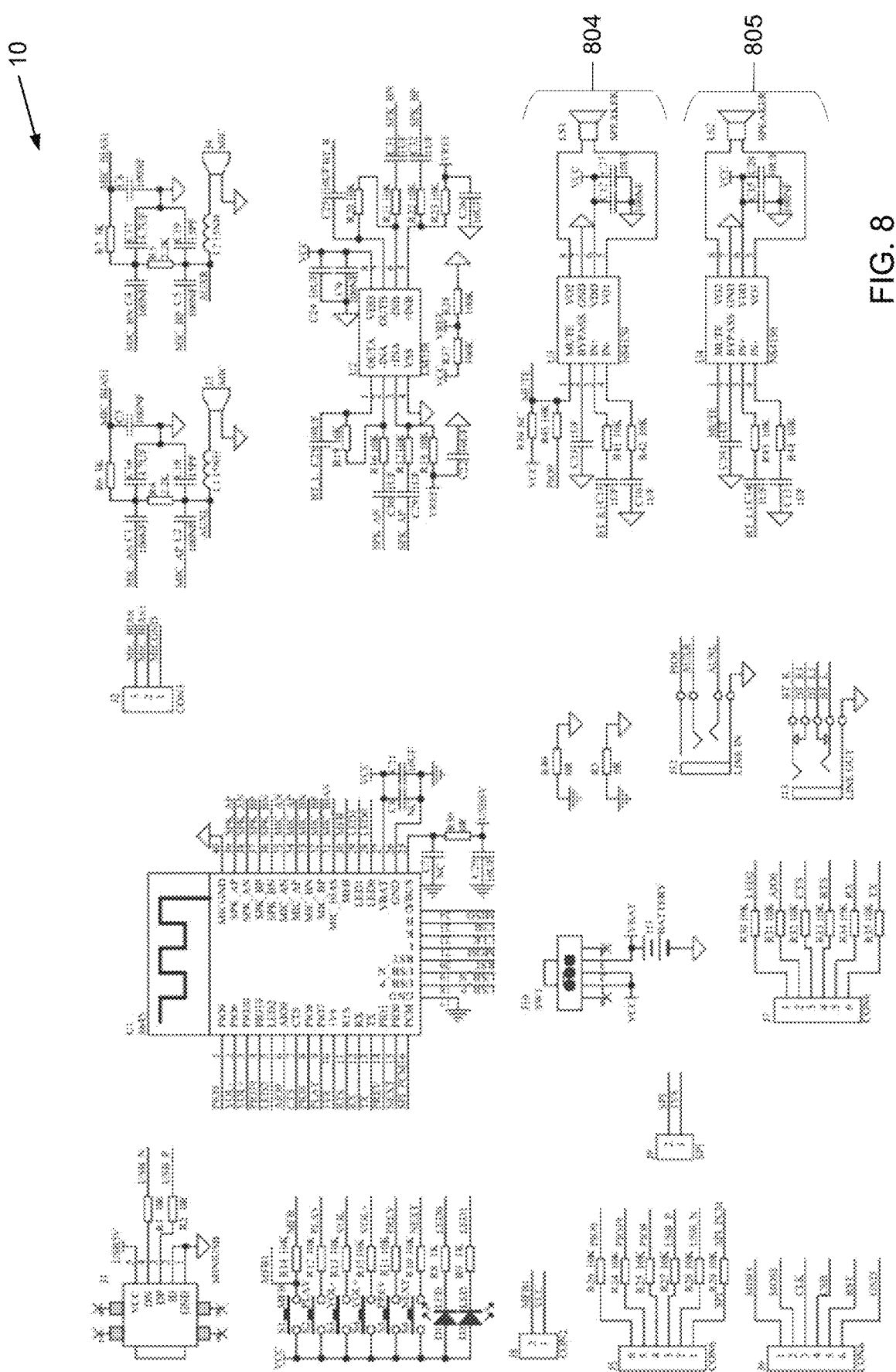
FIG. 8 is a schematic diagram of electrical circuitry implementing a modular headphone system.

In the disclosed example the electronics necessary for the music mode and the HP/amp mode is illustrated by FIG. 8, which is a schematic diagram of electrical circuitry implementing a modular headphone system. The circuitry of FIG. 8 includes HP/amp audio driver 805 to drive speaker 35 of can 20 and music audio driver 804 to drive speaker 34 of can 22. Alternatively, the electronics necessary for both the music mode and the HP/amp mode can be found in either of can 20 or can 22 with wires making connections to the speaker on the can on the opposite side. In either case it is preferred that various switches, buttons, indicators be located on both can 20 and can 22 to keep functions separate and not have the switches, buttons and indicators too close to one another.

It is preferred that headphone 10 includes a microphone to detect environmental noise. Microphones can be situated in either one of or both earpieces 14, 16. FIG. 6 shows a volume control switch 84 that, in this example, controls the volume for both earpieces 14, 16 in the music mode and also controls the amplification of low level noise in the HP/amp mode, such as when an industrial setting or while hunting or at a shooting range. FIG. 3 shows a mode switch 86 that activates a hunting mode in which the user can adjust volume needed to be heard. In one embodiment, pressing the up arrow button of mode switch 86 causes the headphone 10 to enter a hunting mode and to raise the threshold for amplifying sounds greater than the threshold. Pressing the down arrow button of mode switch 86 causes the headphone to lower the threshold for sound amplification. With renewed reference to FIG. 5, various controls and optional visual indicators provide the user with the capability to control the features of the headphone 10. A Bluetooth button 55 enables the user to pair the headphone with a Bluetooth signal source. An appropriately positioned blue tooth indicator LED blinks white during pairing; shows steady white when paired and is otherwise off when not working. An HP button 57 provides the user control over toggling between HP/amp mode and music mode. A conveniently located HP indicator shows white when working, red when battery state is low and is off when the headphone 10 is not working. When the HP button 57 is pressed, the HP indicator shows red for 3 seconds and then turns off to save power. An NC button 59 enables the user to toggle Noise Cancelling (NC) on and off. A proximately located NC indicator shows white for 3 seconds when noise cancelling is activated and is off when noise cancelling is off. Control buttons 55, 57, and 59 are turned on with a long press and off with a short press. Alternatively a simple toggling of the function can be implemented. Optionally, a 3.5 mm input 61 provides the user the capability to enjoy music when the headphone has no connectivity to Bluetooth. When active, headphone 10 will automatically shut off HP protection, Bluetooth, and noise cancelling. Noise level amplification can be provided by different techniques, with sound compression currently preferred. The electronics preferably is designed to stop amplification when the level of external sound,—an impulse sound or ambient sounds as described above, for example,— exceeds a threshold of about 82 dB or as adjusted in hunter mode; this is true for both modes. Therefore, in the HP/amp mode, sound amplification is quickly shut down in response to an impulse sound such as a gunshot and quickly returns to sound amplification, preferably within 2 ms. It is preferred that both left and right earpieces 14, 16 using both HP/amp ear cup 24 and music ear cup 26 achieve a noise reduction rating (NRR) of at least 22 and preferably 28-30. When in the music mode, it is preferred that the music, or other sound being delivered to the user, be paused upon receipt of a telephone call and automatically turned back on upon completion of the telephone call. Conventional noise cancellation, preferably of at least 20 dB, can be provided for either or both the music mode and the HP/amp mode.

The above descriptions may have used terms such as above, below, top, bottom, over, under, et cetera. These terms may be used in the description and claims to aid understanding what is being disclosed and not used in a limiting sense.

While implementations of the technology are disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the technology disclosed and the scope of the following claims. For example, different materials may be used to construct the headphone and its components, switches and controls can be placed in different configurations and/or positions. Some controls may be merged into single controls for simplification. Aural feedback can replace or augment visual indicators. Other colors and states for visual indicators may be used. Component values are recommendations, but can differ among implementations and individual units of a particular implementation due to manufacturing tolerances. Components may be sourced from different suppliers that provide parts of analogous functionality under different brand or type names.

One or more elements of one or more claims can be combined with elements of other claims. Any and all patents, patent applications and printed publications referred to above are incorporated by reference.

What is claimed is:

1. A modular headphone system to provide a wearer configurable choices of hearing protection and quality sound delivery for music and programming, the system comprising:
   a headband; and
   an earpiece mounted to the headband, the earpiece comprising:
      a can secured to the headband, the can comprising:
         a speaker,
         a microphone that captures ambient environmental sound surrounding the environment,
         an amplifier circuit that amplifies a signal from the microphone including the captured ambient environmental sound, thereby providing an amplified ambient environmental sound, and
         circuitry that ceases the amplification of the ambient environmental sound by the amplifier circuit in response to an impulse sound exceeding an adjustable threshold, thereby enabling the headphone system to capture and amplify environmental sounds from the ambient environment prior to detection of the impulse sound and to, upon detection of the impulse sound, protect a wearer's hearing by ceasing the amplification of the ambient environmental sound including the impulse sound;
      a removable and replaceable music ear cup removably mountable to the can to overlie the speaker; and
      a removable and replaceable hearing protection/sound amplification (HP/amp) ear cup removably mountable to the can to overlie the speaker,
   wherein the circuitry resumes the amplification of the ambient environmental sound by the amplifier circuit within 2 ms of the ceasing of the amplification of the ambient environmental sound including the impulse sound.

2. The modular headphone system according to claim 1, wherein the can comprises a can body, the can body comprising:
   a circumferentially-extending side wall surrounding the speaker; and
   a circumferentially-extending open region defined between the speaker and the side wall.

3. The modular headphone system according to claim 2, wherein the HP/amp ear cup comprises:
   a sound absorbing element within the circumferentially-extending open region; and
   a sound absorbing layer overlying the sound absorbing element and the speaker.

4. The modular headphone system according to claim 2, wherein each of the music ear cup and the HP/amp ear cup comprises:
   an understructure having a circumferentially-extending outer portion defining an open region aligned with the speaker; and a cushion structure mounted to the understructure, the cushion structure defining an ear-receiving open region aligned with the open region of the understructure.

5. The modular headphone system according to claim 4, wherein the cushion structure comprises:
a resilient, circumferentially extending, cushion structure body having an inner, circumferentially extending surface, an outer, circumferentially extending surface, and a face surface joining the inner and outer circumferentially extending surfaces; and
a body cover covering the inner and outer circumferentially extending surfaces and the face surface.

6. The modular headphone system according to claim 5, wherein the cushion structure body is made of polyurethane memory foam and the body cover is made of polyurethane synthetic leather.

7. The modular headphone system according to claim 5, wherein the cushion structure further comprises a sound-permeable cover overlying the open region of the understructure.

8. The modular headphone system according to claim 4, wherein the HP/amp ear cup comprises:
a sound absorbing element within the circumferentially-extending open region; and
a sound absorbing layer overlying the sound absorbing element and the speaker.

9. The modular headphone system according to claim 8, where the sound absorbing element is made of one or more of polyurethane foam, cotton, melamine, or composite materials.

10. The modular headphone system according to claim 8, where the sound absorbing element is 5 mm to 15 mm thick.

11. The modular headphone system according to claim 8, where the sound absorbing layer is made of one or more of polyurethane foam, cotton, melamine, or composite materials and the sound absorbing layer is 2 mm to 4 mm thick.

12. The modular headphone system according to claim 1, wherein the circuitry ceases the sound amplification in response to the impulse sound exceeding a level of 82 dB.

13. The modular headphone system according to claim 1, further including a toggle enabling a user to selectively activate capability of the circuitry to cease amplification upon detection of the impulse sound.

14. The modular headphone system of claim 1, wherein the adjustable threshold is adjustable by the wearer.

15. A headphone system comprising:
a headband; and
an earpiece mounted to the headband, the earpiece comprising:
a can comprising a speaker, the can being secured to the headband; and
a hearing protection/sound amplification (HP/amp) ear cup mounted to the can to overlie the speaker,
wherein the can comprises a can body, the can body comprising:
a circumferentially-extending side wall surrounding the speaker; and
a circumferentially-extending region defined within an inner region defined between the speaker and the side wall,
wherein the ear cup comprises:
a sound-absorbing element within the circumferentially-extending region;
a sound-absorbing layer overlying the sound-absorbing element and the speaker; and
an outer ear cup structure, configured to engage a user's ear, mounted to the can and overlying the sound-absorbing layer,
wherein the can further comprises:
a microphone that captures ambient environmental sound surrounding the environment,
an amplifier circuit that amplifies a signal from the microphone including the captured ambient environmental sound, thereby providing an amplified ambient environmental sound, and
circuitry that ceases the amplification of the ambient environmental sound by the amplifier circuit in response to an impulse sound exceeding an adjustable threshold, thereby enabling the headphone system to capture and amplify environmental sounds from the ambient environment prior to detection of the impulse sound and to, upon detection of the impulse sound, protect a wearer's hearing by ceasing the amplification of the ambient environmental sound including the impulse sound, and
wherein the circuitry resumes the amplification of the ambient environmental sound by the amplifier circuit within 2 ms of the ceasing of the amplification of the ambient environmental sound including the impulse sound.

16. The headphone system according to claim 15, wherein the outer ear cup structure comprises:
an understructure having a circumferentially-extending outer portion defining an open region aligned with the speaker; and
cushion structure mounted to the understructure, the cushion structure defining an ear-receiving open region aligned with the open region of the understructure,
wherein the cushion structure further is comprises:
a resilient, circumferentially extending, cushion structure body having an inner, circumferentially extending surface, an outer, circumferentially extending surface, and a face surface joining the inner and outer circumferentially extending surfaces;
a body cover covering the inner and outer circumferentially extending surfaces and the face surface; and
a sound-permeable cover overlying the open region of the understructure.

* * * * *